US006984617B2

(12) United States Patent
Holland et al.

(10) Patent No.: US 6,984,617 B2
(45) Date of Patent: Jan. 10, 2006

(54) FRAGRANCE RELEASE

(75) Inventors: Lynette Anne Makins Holland, Watford (GB); Jerome Anthony Janszen, Cincinnati, OH (US); Peter James Malton, Staines (GB); David John Pung, Loveland, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 225 days.

(21) Appl. No.: 10/422,888

(22) Filed: Apr. 24, 2003

(65) Prior Publication Data

US 2003/0232730 A1    Dec. 18, 2003

Related U.S. Application Data

(60) Provisional application No. 60/376,028, filed on Apr. 26, 2002.

(51) Int. Cl.
  *C11D 17/04*  (2006.01)
(52) U.S. Cl. ............................ 510/441; 510/101; 512/4
(58) Field of Classification Search ................ 510/101, 510/441; 512/4

See application file for complete search history.

(56) References Cited

U.S. PATENT DOCUMENTS

| 4,428,869 | A |   | 1/1984  | Munteanu et al. |
| 5,066,419 | A | * | 11/1991 | Walley et al. ............... 510/396 |
| 5,238,915 | A | * | 8/1993  | Fuwa et al. .................... 512/4 |
| 5,246,611 | A |   | 9/1993  | Trinh et al. |
| 5,384,186 | A | * | 1/1995  | Trinh .......................... 442/96 |
| 5,723,420 | A | * | 3/1998  | Wei et al. ................... 510/101 |

FOREIGN PATENT DOCUMENTS

| FR | 2 774 389   |   | 2/1998 |
| WO | WO 98/27261 | * | 6/1998 |
| WO | WO99/21532  |   | 5/1999 |
| WO | WO 01/40430 | * | 6/2001 |

* cited by examiner

*Primary Examiner*—John R. Hardee
(74) *Attorney, Agent, or Firm*—Kenya T. Pierre; Brian M. Bolam; Tara M. Rognell

(57) ABSTRACT

Compositions and personal care articles are described comprising a complexed perfume and a coating material which acts to retain the perfume in the complexed state and to keep out other competing materials.

17 Claims, No Drawings

FRAGRANCE RELEASE

CROSS REFERENCE TO RELATED APPLICATION

This application claims the benefit under 35 USC 119(e) to U.S. Application Ser. No. 60/376,028, filed Apr. 26, 2002.

TECHNICAL FIELD

The present invention relates to the delivery of fragrances to skin and/or hair. In a first aspect, the invention concerns compositions achieving controlled delivery of fragrances. In a second and third aspect, the invention concerns personal care products comprising substrates and compositions achieving controlled delivery of fragrances.

BACKGROUND OF THE INVENTION

Humans have applied scents and fragrances to their skins since ancient times. Originally, these aesthetically pleasing materials were commonly isolated in raw form as gums, resins or essential oils from their natural sources, such as the bark, roots, leaves and fruit of indigenous plants. These gums, resins and oils were directly applied to the body or were diluted with water or other solvent, including, in some cases, wine, then applied by means of the delivery vehicle. With the advent of modern chemistry, the individual components responsible for the odour properties of these resins, gums and oils were isolated and subsequently characterised, enabling the manufacture of "perfumes vehicles", such as fine fragrances and aftershave lotions.

Traditional perfumes may comprise perfume oils derived from the sources discussed above and these oils may have a mixture of boiling points varying from low to high. It is self-evident that the highly volatile (low boiling), so-called "top note" constituents are short-lived once deposited onto a warm surface, such as skin. As a result, if a fragrance were entirely composed of such materials, it would not be very durable. In order to counter this and achieve increased fragrance substantivity and longevity, traditional perfumes tended to comprise high levels of lower volatility, so-called "middle note" and "base note" fragrance oils. This, however, has certain disadvantages: a consumer who tests a scent in a store often devotes only a short period of time to the evaluation, during which mainly the top notes of the scent will be in evidence, whereas, having purchased the product, that consumer may then be disappointed with the residual middle and base notes which were less in evidence during their test. In addition, the high volatility of top notes and their corresponding low longevity mean that they are traditionally included at low levels (since they are short lived)—a de facto restriction on the freedom of the perfumer to formulate a fragrance.

To counter these disadvantages of traditional perfumes, it has been proposed to generate complexes (hereafter "fragrance-releasing complexes") of perfumes and other materials (hereafter "entrapment materials"), which depress the volatility of the fragrances and allow a more controlled release over time—reference is made to WO 99/21532. The production of such non-volatile complexes allows the perfume to be retained on skin/hair until such times as its release is triggered. Entrapment materials which have been proposed for complex formation in the prior art are discussed hereinbelow. The "trigger" referred to may be a single factor such as externally applied moisture or pH change, or, in the case of skin, a combination of factors such as sweat and its components—for example urea, lactic acid and moisture as well as sebum components, such as cholesterol.

At least in theory, the use of fragrance-releasing complexes allows the possibility of selectively retaining perfumes of a given volatility, such as the elusive top-note fragrances, thereby reducing or avoiding some of the disadvantages discussed in the above paragraphs. This would open up a world of new possibilities: not only could fragrances be designed to have longer lasting top notes, but the evolution of a fragrance post application could be changed to give unique character combinations during the so-called "dry down", i.e. a uniquely changing character with time.

In practice, however, retention, particularly of the top-note scents, is not easy to achieve. While not wishing to be bound by any theory, there appear to be a number of reasons why this is so. In the first place, entrapment materials do not tend to differentiate between top, middle and bottom note fragrances, so that, in a given fragrance, all notes will be complexed. Put another way, increased perfume oil volatility does not appear to equate in any significant way to increased ability to complex. Rather, it would appear that, if all other factors are equal, the degree of complexation of a perfume raw material of given volatility is roughly proportional to its proportion in the mixture. To counteract this effect, it would, of course, be possible to increase the amount of top note oils present, but that could radically alter the oil balance, thereby changing the entire nature of the fragrance. It would also place significant restrictions on perfumers as to what they could put into their fragrances, similarly to the way that, in the past, the high volatility of top notes has lead to inclusion of low levels of top notes in fragrances. A second factor which may limit the capture and retention of top note fragrance oils by entrapment materials may be the presence in many traditional fragrances of certain non-aqueous solvents, such as certain alcohols, which may interfere with the entrapment materials.

Ideally, the present invention will achieve improved fragrance retention by fragrance-releasing complexes.

Ideally, the present invention will also selectively improve capture and retention of top note fragrances within fragrance-releasing complexes.

Ideally, the present invention will also provide personal care articles comprising compositions which achieve the above objectives.

SUMMARY OF THE INVENTION

According to a first aspect of the invention, a composition is provided comprising a fragrance-releasing complex of an entrapment material and a fragrance; and an encapsulation material, wherein the weight ratio of fragrance-releasing complex to encapsulation material is greater than 1.

As used herein, the term "encapsulation material" includes any material which is capable of coating the fragrance releasing complex to retain the fragrance in the complexed state.

As used herein, the term "fragrance-releasing complex" includes fragrance which is reversibly associated with an entrapment material.

As used herein, the term "entrapment material" includes any material which, when associated with a fragrance, has the effect of suppressing the volatility of that fragrance and delaying its evaporation.

As used herein, the term "associated" includes chemical and physical linkage. The term "chemical linkage" includes covalent, ionic, hydrogen and other types of chemical bond;

the term "physical linkage" includes linkage by Van der Waals force and other types of physical bond.

The word "reversibly" used to qualify "associated" includes associations which can be broken down so that the fragrance is released from the entrapment material; breakdown is effected by a "trigger" as discussed above.

As used herein the term "fragrance" includes mixtures of perfume raw materials (PRMs) that are used to impart an overall pleasant odour profile to a composition, particularly a cosmetic composition. A wide variety of chemicals are useful as PRMs, including materials such as aldehydes, ketones and esters, which may be synthetic or may be derived from naturally occurring plant or animal sources. Lists of PRMs can be found in Journals used by those in the art such as "Perfume and Flavourist" or "Journal of Essential Oil Research". As used herein, the term "perfume raw material" includes oil which is liquid at a temperature of 25° C. and 1 atmosphere pressure, has a ClogP value greater than about 0.1, preferably greater than about 0.5 and more preferably greater than about 1.0.

As used herein, the term "ClogP" means the logarithm to base 10 of the octanol/water partition coefficient (P). The octanol/water partition coefficient of a PRM is the ratio between its equilibrium concentrations in octanol and water. Given that this measure is a ratio of the equilibrium concentration of a PRM in a non-polar solvent (octanol) with its concentration in a polar solvent (water), ClogP is also a measure of the hydrophobicity of a material—the higher the ClogP value, the more hydrophobic the material. ClogP values can be readily calculated from a program called "CLOGP" which is available from Daylight Chemical Information Systems Inc., Irvine, Calif., USA. Octanol/water partition coefficients are described in more detail in U.S. Pat. No. 5,578,563.

In a further advantageous aspect, the weight ratio of fragrance-releasing complex to encapsulation material within the composition according to the invention is in the range 1:0.1 to 1:0.9; preferably it is in the range 1:0.2 to 1:0.8 and more preferably, it is in the range 1:0.35 to 1:0.71.

The encapsulation material according to the invention may comprise a non-ionic surfactant. Preferably, the non-ionic surfactant comprises block copolymers of ethylene oxide and propylene oxide, polyalkylene oxide siloxanes, partially or fully hydrogenated polyoxyethylene castor oil ethers or polyoxyethylene hardened castor oil ethers, sorbitan esters of long chain fatty acids, polyethoxylated fatty alcohol surfactants, glycerol mono-fatty acid esters, fatty acid esters of polyethylene glycol, fluorocarbon surfactants and mixtures thereof. Advantageously, the non-ionic surfactant has a molecular weight above 400.

The entrapment material according to the invention may comprise capsules, microcapsules, nanocapsules, liposomes, film-formers, cyclic oligosaccharides, materials capable of transforming fragrances into pro-perfumes and mixtures thereof.

The fragrance comprised within the fragrance-releasing complex may be a first fragrance and may advantageously comprise perfume raw materials, at least 80% of which, preferably at least 90% of which, have a boiling point of less than or equal to 300° C.

More advantageously, the first fragrance comprises perfume raw materials at least 50% of which, preferably at least 60% of which, more preferably at least 75% of which have a ClogP value of greater than or equal to 3.

Even more advantageously, the first fragrance comprises perfume raw materials having a molecular weight of less than 200.

The composition according to the invention may also comprise a second fragrance. Advantageously, the second fragrance comprises perfume raw materials, at least 80% of which, preferably at least 90% of which have a boiling point above 300° C.

More advantageously, the second fragrance comprises perfume raw materials having a molecular weight of 200 or more.

The composition according to the invention advantageously comprises at least 50% wt, preferably at least 70% wt and more preferably 75 to 90% wt water. In such a case, the composition may also comprise less than 20% wt, preferably between 5 and 15% wt of a volatile, non-aqueous solvent.

According to a second aspect of the invention, a personal care article is provided comprising a substrate and a composition as defined above. Preferably, the weight ratio of substrate to composition is in the range 1:0.1 to 1:10. More preferably, it is in the range 1:5 to 1:3.1.

According to a third aspect of the invention, a personal care article is provided comprising a substrate and a composition, the composition comprising a fragrance-releasing complex and more than 50% wt water, preferably between 80 and 90% wt water.

The substrate comprised within the personal care article according to the second or third aspect of the invention may advantageously be a nonwoven; more advantageously, the personal care article according to the second or third aspects of the invention may be packaged as a wet wipe in packaging that retains moisture.

DETAILED DESCRIPTION

Unless otherwise indicated, all percentages of compositions referred to herein are weight percentages and all ratios are weight ratios.

Unless otherwise indicated, all boiling points referred to herein are determined at standard pressure of 760 mm Hg.

Unless otherwise indicated, all molecular weights are weight average molecular weights.

Unless otherwise indicated, the content of all literature sources referred to within this text are incorporated herein in full by reference.

Except where specific examples of actual measured values are presented, numerical values referred to herein should be considered to be qualified by the word "about".

The composition according to the invention may comprise from 0.01 to 10% wt of entrapment material, preferably from 0.01 to 5% wt and more preferably from 0.1 to 2.5% wt entrapment material.

Entrapment materials which may be used according to the invention include polymers; capsules, microcapsules and nanocapsules; liposomes; film formers; cyclic oligosaccharides; materials capable of transforming the fragrances into so-called pro-perfumes and mixtures of these. Preferred are materials capable of transforming fragrances into pro-perfumes, cyclic oligosaccharides and mixtures thereof. Highly preferred are cyclic oligosaccharides and mixtures thereof.

The entrapment material according to the present invention may comprise capsules, micro-capsules or nanocapsules. These materials can be used to control release of fragrance oils, by physically surrounding and entrapping small fragrance oil droplets within a resistant wall. The droplet may then be released when it encounters a trigger in the form of a release agent, for example a dissolution solvent such as water. The water may, for example, be supplied in the form of moisture transpired through the skin. Capsules, microcapsules and nanocapsules are known in the art, for example DE-A-1 268 316, U.S. Pat. No. 3,539,465 and U.S. Pat. No. 3,455,838.

Moisture sensitive capsules, micro-capsules and nanocapsules preferably comprise a polysaccharide polymer. Examples of suitable polymers are dextrins, especially low-viscosity dextrins including maltodextrins. A preferred example of a low viscosity dextrin is one which, as a 50% dispersion in water has a viscosity at 25° C., using a Brookfield Viscometer fitted with an "A" type T-Bar rotating at 20 rpm in helical mode, of 330±20 mpa.s. This dextrin is known as Encapsul 855 and is available from National Starch and Chemicals Ltd. A further example of a polysaccharide that can be used to form the moisture sensitive capsules is gum acacia.

The entrapment material may comprise cyclic oligosaccharides. As used herein, the term "cyclic oligosaccharide" means a cyclic structure comprising six or more saccharide units. Preferred for use herein are cyclic oligosaccharides having six, seven or eight saccharide units and mixtures thereof, more preferably six or seven saccharide units and mixtures thereof and even more preferably seven saccharide units and mixtures thereof. It is common in the art to abbreviate six, seven and eight membered cyclic oligosaccharides to $\alpha$, $\beta$ and $\gamma$ respectively.

The cyclic oligosaccharides for use herein may comprise any suitable saccharide or mixtures of saccharides. Examples of suitable saccharides include, but are not limited to, glucose, fructose, mannose, galactose, maltose and mixtures thereof. It is preferred to use the cyclic oligosaccharides of glucose.

The preferred cyclic oligosaccharides for use herein are $\alpha$-cyclodextrins or $\beta$-cyclodextrins, or mixtures thereof, and the most preferred cyclic oligosaccharides for use herein are $\beta$-cyclodextrins. These cyclic molecules are capable of releasably entrapping "guest" molecules in their internal cavities, typically in the ratio of cyclodextrin molecule to guest molecule of 1:1, though the ratio may also be higher or lower, depending on the sizes of the cavity and the guest molecule.

The cyclic oligosaccharide, or mixture of cyclic oligosaccharides, for use herein may be substituted by any suitable substituent or mixture of substituents. Suitable substituents include, but are not limited to, alkyl groups, hydroxyalkyl groups, dihydroxyalkyl groups, (hydroxyalkyl)alkylenyl bridging groups such as cyclodextrin glycerol ethers, aryl groups, maltosyl groups, allyl groups, benzyl groups, alkanoyl groups, cationic cyclodextrins such as those containing 2-hydroxy-3-(dimethylamino) propyl ether, quaternary ammonium groups, anionic cyclodextrins such as carboxyalkyl groups, sulphobutylether groups, sulphate groups, and succinylates; amphoteric cyclodextrins; and mixtures thereof. The substituents may be saturated or unsaturated, straight or branched chain moieties. Preferred substituents include saturated and straight chain alkyl groups, hydroxyalkyl groups and mixtures thereof. Preferred alkyl and hydroxyalkyl substituents are selected from $C_1$–$C_8$ alkyl or hydroxyalkyl groups or mixtures thereof, more preferred alkyl and hydroxyalkyl substituents are selected from $C_1$–$C_6$ alkyl or hydroxyalkyl groups or mixtures thereof, even more preferred alkyl and hydroxyalkyl substituents are selected from $C_1$–$C_4$ alkyl or hydroxyalkyl groups and mixtures thereof. Especially preferred alkyl and hydroxyalkyl substituents are propyl, hydroxypropyl, ethyl and methyl, more especially hydroxypropyl and methyl and even more preferably methyl.

Preferred cyclic oligosaccharides for use in the present invention are unsubstituted, or are substituted by only saturated straight chain alkyl, or hydroxyalkyl, substituents. Therefore, preferred examples of cyclic oligosaccharides for use herein are $\alpha$-cyclodextrin, $\beta$-cyclodextrin, methyl-$\alpha$-cyclodextrin, methyl-$\beta$-cyclodextrin, hydroxypropyl-$\alpha$-cyclodextrin and hydroxypropyl-$\beta$-cyclodextrin, or mixtures thereof. More preferred examples of cyclic oligosaccharides for use herein are methyl-$\alpha$-cyclodextrin and methyl-$\beta$-cyclodextrin. These are available from Wacker-Chemie GmbH, Hanns-Seidel-Platz 4, München, Germany under the tradenames Alpha W6 M and Beta W7 M respectively. Most preferred is methyl-$\beta$-cyclodextrin.

Methods of modifying cyclic oligosaccharides are well known in the art. For example, see *"Methods of Selective Modifications of Cyclodextrins" Chemical Reviews* (1998) Vol. 98, No. 5, pp 1977–1996, Khan et al and U.S. Pat. No. 5,710,268.

In addition to identifying the preferred substituents themselves (as outlined above), it is also preferred that the cyclic oligosaccharides have an average degree of substitution of between 1.6 and 2.8, wherein the term "degree of substitution" means the average number of substituents per saccharide unit. More preferably, the cyclic oligosaccharides for use herein have an average degree of substitution of from about 1.7 to about 2.0. The average number of substituents can be determined using common Nuclear Magnetic Resonance techniques known in the art.

The cyclic oligosaccharides are preferably soluble in both water and ethanol. As used herein, "soluble" means at least about 0.1 g of solute dissolves in 100 ml of solvent, at 25° C. and 1 atm of pressure. Preferably, the cyclic oligosaccharides for use herein have a solubility of at least about 1 g/100 ml, at 25° C. and 1 atm of pressure.

The entrapment material according to the invention may comprise material capable of transforming fragrances into so-called pro-perfumes or profragrances. Pro-perfumes are fragrances which have been reversibly modified to suppress the volatility of that fragrance and delay its evaporation. Pro-fragrances may be synthesised from a given fragrance by conversion of that fragrance into a chemical species or reactive chemical form which releases the fragrance when the pro-fragrance is subjected to the proper conditions triggering breakdown, for example by hydrolysis. Synthesis may comprise reacting the fragrance with more than one type of entrapment material. These entrapment materials may comprise any one or more of a number of chemical groups such as acetal, ketal, orthoester or orthocarbonates. Depending on the pro-fragrance chosen, the trigger may range from contact with the acid mantle of the human skin or enzymes in the human skin to a shift in reaction equilibrium, a pH change or exposure to light. Once released, the fragrance has its original characteristics. Non-limiting examples of entrapment materials (and corresponding pro-perfumes) which may be included in compositions according to the present invention are described in WO 98/47477, WO 99/43667, WO 98/07405 and WO 98/47478.

Complexes between fragrance and entrapement materials may be formed by kneading the two materials together or, alternatively, they may be formed as solutions in suitable solvents. The solvent may be water or another appropriate solvent, though reference is made to the limitations concerning volatile, non-aqueous solvents, discussed below. Preferably, the solvent is water and the complex is formed by bringing together appropriate amounts of perfume and entrapment material in the solvent.

The presence of encapsulation material in the ratio range according to the invention acts to retain fragrance in the complexed state, especially in the preferred ranges. Without wishing to be bound by any theory, it is believed that this has at least two reasons: in the first place, the encapsulation material coats the complex to form a physical barrier which prevents fragrance from leaving the complex or other materials from displacing the fragrance; secondly, the encapsulation material may also serve to prevent other materials from displacing the fragrance by solubilising those materials. The encapsulation material may be used to retain top note fragrances in the complexed state, though the effect is not limited to retention of top notes.

The encapsulation material must be capable of removal to expose the fragrance-releasing complex to appropriate triggers to activate fragrance release. Removal may be achieved by means of external influences—in the case of non-ionic surfactants, the combination of the presence of moisture found on the surface of human skin and/or friction may be employed to expose the fragrance-releasing complex to appropriate triggers.

The composition according to the invention may comprise from 0.01 to 10% wt encapsulation material, preferably from 0.01 to 4% wt and more preferably from 0.1 to 1% wt encapsulation material.

Nonlimiting examples of encapsulation materials which may be used in compositions according to the invention include non-ionic surfactants.

Nonlimiting examples of nonionic surfactants include block copolymers of ethylene oxide and propylene oxide. Suitable block polyoxyethylene-polyoxypropylene polymeric surfactants include those based on ethylene glycol, propylene glycol, glycerol, trimethylolpropane and ethylenediamine as the initial reactive hydrogen compound. Certain of the block polymer surfactant compounds designated Pluronic® and Tetronic® by the BASF-Wyandotte Corp., Wyandotte, Mich., are readily available. Nonlimiting examples of compatible surfactants of this type include Pluronic Surfactants with the general formula $H(EO)_n(PO)_m(EO)_nH$, wherein EO is an ethylene oxide group, PO is a propylene oxide group, and n and m are numbers that indicate the average number of the groups in the surfactants. Typical examples suitable Pluronic surfactants are:

| Name | Average MW | Average n | Average m |
|---|---|---|---|
| L-101 | 3,800 | 4 | 59 |
| L-81 | 2,750 | 3 | 42 |
| L-44 | 2,200 | 10 | 23 |
| L-43 | 1,850 | 6 | 22 |
| F-38 | 4,700 | 43 | 16 |
| P-84 | 4,200 | 19 | 43, |
| and mixtures thereof. | | | |

Suitable Tetronic Surfactants may have the general formula:

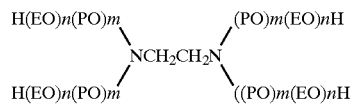

wherein EO, PO, n, and m have the same meanings as above. Typical examples of suitable Tetronic surfactants are:

| Name | Average MW | Average n | Average m |
|---|---|---|---|
| 901 | 4,700 | 3 | 18 |
| 908 | 25,000 | 114 | 22, |
| and mixtures thereof. | | | |

"Reverse" Pluronic and Tetronic surfactants have the following general formulas:

Reverse Pluronic Surfactants $H(PO)_m(EO)_n(PO)_mH$

Reverse Tetronic Surfactants

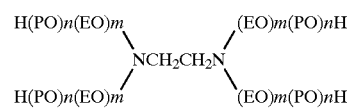

wherein EO, PO, n, and m have the same meanings as above. Typical examples of suitable Reverse Pluronic and Reverse Tetronic surfactants are:

Reverse Pluronic surfactants are:

| Name | Average MW | Average n | Average m |
|---|---|---|---|
| 10 R5 | 1,950 | 8 | 22 |
| 25 R1 | 2,700 | 21 | 6 |

Reverse Tetronic surfactants

| Name | Average MW | Average n | Average m |
|---|---|---|---|
| 130 R2 | 7,740 | 9 | 26 |
| 70 R2 | 3,870 | 4 | 13 |
| and mixtures thereof. | | | |

Another class of nonionic surfactants which may be included in compositions according to the invention are the polyalkyleneoxide polysiloxanes such as those having a dimethyl polysiloxane hydrophobic moiety and one or more hydrophilic polyalkylene side chains and have the general formula:

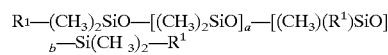

wherein a+b are from about 1 to about 50, preferably from about 3 to about 30, more preferably from about 10 to about 25, and each $R^1$ is the same or different and is selected from the group consisting of methyl and a poly(ethyleneoxide/propyleneoxide) copolymer group having the general formula:

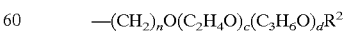

with at least one $R^1$ being a poly(ethyleneoxide/propyleneoxide) copolymer group, and wherein n is 3 or 4, preferably 3; total c (for all polyalkyleneoxy side groups) has a value of from 1 to about 100, preferably from about 6 to about 100; total d is from 0 to about 14, preferably from 0 to about 3; and more preferably d is 0; total c+d has a value of from about 5 to about 150, preferably from about 9 to about 100 and each $R^2$ is the same or different and is selected from the group consisting of hydrogen, an alkyl having 1 to 4 carbon atoms, and an acetyl group, preferably hydrogen and methyl group.

Examples of this type of surfactants are the Silwet® surfactants which are available OSi Specialties, Inc., Danbury, Conn. Representative Silwet surfactants are as follows.

| Name | Average MW | Average a + b | Average total c |
|---|---|---|---|
| L-7608 | 600 | 1 | 9 |
| L-7607 | 1,000 | 2 | 17 |
| L-77 | 600 | 1 | 9 |
| L-7605 | 6,000 | 20 | 99 |
| L-7604 | 4,000 | 21 | 53 |
| L-7600 | 4,000 | 11 | 68 |
| L-7657 | 5,000 | 20 | 76 |
| L-7602 | 3,000 | 20 | 29 |

The molecular weight of the polyalkyleneoxy group ($R^1$) is less than or equal to about 10,000. Preferably, the molecular weight of the polyalkyleneoxy group is less than or equal to about 8,000, and most preferably ranges from about 300 to about 5,000. Thus, the values of c and d can be those numbers which provide molecular weights within these ranges. However, the number of ethyleneoxy units ($-C_2H_4O$) in the polyether chain ($R^1$) must be sufficient to render the polyalkyleneoxide polysiloxane water dispersible or water soluble. If propyleneoxy groups are present in the polyalkylenoxy chain, they can be distributed randomly in the chain or exist as blocks. Preferred Silwet surfactants are L-7600, L-7602, L-7604, L-7605, L-7657, and mixtures thereof.

The preparation of polyalkyleneoxide polysiloxanes is well known in the art. Polyalkyleneoxide polysiloxanes of the present invention can be prepared according to the procedure set forth in U.S. Pat. No. 3,299,112. Typically, polyalkyleneoxide polysiloxanes of the surfactant blend of the present invention are readily prepared by an addition reaction between a hydrosiloxane (i.e., a siloxane containing silicon-bonded hydrogen) and an alkenyl ether (e.g., a vinyl, allyl, or methallyl ether) of an alkoxy or hydroxy end-blocked polyalkylene oxide). The reaction conditions employed in addition reactions of this type are well known in the art and in general involve heating the reactants (e.g., at a temperature of from about 85° C. to 110° C.) in the presence of a platinum catalyst (e.g., chloroplatinic acid) and a solvent (e.g., toluene).

Another class of non-ionic surfactants which may be used in compostions according to the invention include polyoxyethylene castor oil ethers or polyoxyethylene hardened castor oil ethers or mixtures thereof, which are either partially or fully hydrogenated. These ethoxylates have the following general formulae:

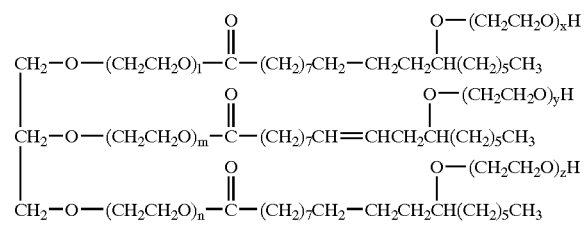

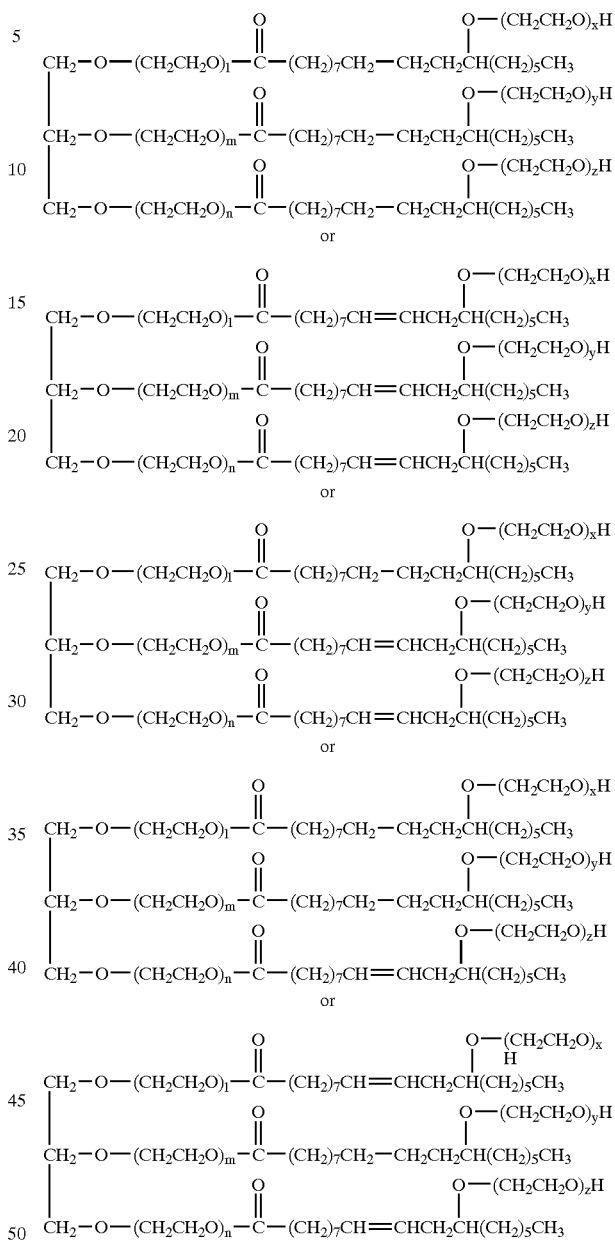

These ethoxylates can be used alone or in any mixture thereof. The average ethylene oxide addition mole number (i.e., l+m+n+x+y+z in the above formula) of these ethoxylates is generally from about 7 to about 100, and preferably from about 20 to about 80. Castor oil surfactants are commerically available from Nikko under the trade names HCO 40 and HCO 60 and from BASF under the trade names Cremphor™ RH 40, RH 60, and CO 60.

Another class of non-ionic surfactants which may be used in compostions according to the invention include sorbitan esters of long-chain fatty acids, such as those having long-chain fatty acid residues with 14 to 18 carbon atoms, preferably 16 to 18 carbon atoms. Furthermore, the esterification degree of the sorbitan polyesters of long-chain fatty acids is preferably 2.5 to 3.5, more preferably 2.8 to 3.2.

Typical examples of these sorbitan polyesters of long-chain fatty acids are sorbitan tripalmitate, sorbitan trioleate, and sorbitan tallow fatty acid triesters.

Other suitable sorbitan ester surfactants include sorbitan fatty acid esters, particularly the mono-and tri-esters of the formula:

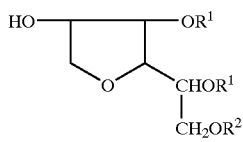

wherein $R^1$ is H or

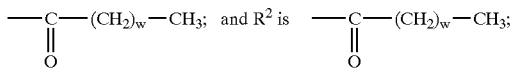

and w is from about 10 to about 16.

Further suitable sorbitan ester surfactants include polyethoxylated sorbitan fatty acid esters, particularly those of the formula:

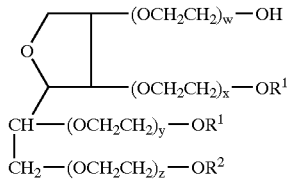

wherein $R^1$ is H or

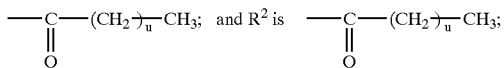

u is from about 10 to about 16 and average (w+x+y+z) is from about 2 to about 20. Preferably, u is 16 and average (w+x+y+z) is from about 2 to about 4.

Another class of non-ionic surfactants which may be used in compostions according to the invention include polyethoxylated fatty alcohol surfactants such as those having the formula:

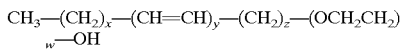

wherein w is from about 0 to about 100, preferably from about 0 to about 80; y is 0 or 1; x is from about 1 to about 10; z is from about 1 to about 10; x+z+y=11 to 25, preferably 11 to 23.

Branched (polyethoxylated) fatty alcohols having the following formula may also be incorporated into the present compositions:

wherein R is a branched alkyl group of from about 10 to about 26 carbon atoms and w is as specified above.

Another class of non-ionic surfactants which may be used in compostions according to the invention include glycerol mono-fatty acid esters, particularly glycerol mono-stearate, oleate, palmitate or laurate.

Another class of non-ionic surfactants which may be used in compostions according to the invention include fatty acid esters of polyethylene glycol, particularly those of the following formula:

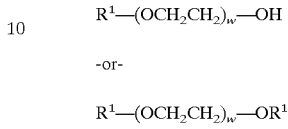

wherein $R^1$ is a stearoyl, lauroyl, oleoyl or palmitoyl residue; w is from about 2 to about 20, preferably from about 2 to about 8.

A further class of non-ionic surfactants which may be used in compostions according to the invention include fluorocarbon surfactants. Fluorocarbon surfactants are a class of surfactants wherein the hydrophobic part of the amphiphile comprises at least in part some portion of a carbon-based linear or cyclic moiety having fluorines attached to the carbon where typically hydrogens would be attached to the carbons together with a hydrophilic head group. Some typical nonlimiting fluorocarbon surfactants include fluorinated alkyl polyoxyalkylene, and fluorinated alkyl esters as well as ionic surfactants. Representative structures for these compounds are given below:

(1) $R_fR(R_1O)_xR_2$
(2) $R_fR—OC(O)R_3$
(3) $R_fR—Y-Z$
(4) $R_fRZ$ wherein $R_f$ contains from about 6 to about 18 carbons each having from about 0 to about 3 fluorines attached. R is either an alkyl or alkylene oxide group which, when present, has from about 1 to about 10 carbons and $R_1$ represents an alkylene radical having from about 1 to about 4 carbons. $R_2$ is either a hydrogen or a small alkyl capping group having from about 1 to about 3 carbons. $R_3$ represents a hydrocarbon moiety comprising from about 2 to about 22 including the carbon on the ester group. This hydrocarbon can be linear, branched or cyclic saturated or unsaturated and contained moieties based on oxygen, nitrogen, and sulfur including, but not limited to ethers, alcohols, esters, carboxylates, amides, amines, thio-esters, and thiols; these oxygen, nitrogen, and sulfur moieties can either interrupt the hydrocabon chain or be pendant on the hydrocarbon chain. In structure 3, Y represents a hydrocarbon group that can be an alkyl, pyridine group, amidopropyl, etc. that acts as a linking group between the fluorinated chain and the hydrophilic head group. In structures 3 and 4, Z represents a cationic, anionic, and amphoteric hydrophilic head groups including, but not limited to carboxylates, sulfates, sulfonates, quaternary ammonium groups, and betaines. Non-limiting commercially available examples of these structures include Zonyl® 9075, FSO, FSN, FS-300, FS-310, FSN-100, FSO-100, FTS, TBC from DuPont and Fluorad™ surfactants FC-430, FC-431, FC-740, FC-99, FC-120, FC-754, FC170C, and FC-171 from the 3M™ company in St. Paul, Minn.

Advantageously, the non-ionic surfactants employed according to the invention have a molecular weight above 400. Below this value, there is a risk that these molecules may act as so-called "molecular wedges" which not only coat the complex, but may also enter the entrapment material and block entry or exit to the fragrances. In other words, entrapment may either be prevented or, where it has occurred, it may cease to be reversible, or release may no longer be controllable. More preferably, the molecular weight is in the range 400 to 20,000.

The first fragrance according to the invention may comprise perfume raw materials of high, medium or low volatility, but preferably of high volatility. These highly volatile fragrances essentially correspond to the "top notes". More preferably, at least 80%, more preferably still at least 90%, of the perfume raw materials have a boiling point of less than 300° C.

Advantageously, the first fragrance is highly hydrophobic, being comprised of perfume raw materials, at least 50%, preferably at least 60%, more preferably at least 75% of which have a ClogP value of at least 3. The ability to complex with entrapment materials, particularly cyclodextrins, appears to increase with the degree of hydrophobicity so that in a kinetic race between fragrances of different polarity, it appears that, when all other parameters are equal, hydrophobic molecules are the more likely to complex than hydrophilic ones. Advantageously, the top note fragrances will therefore comprise PRMs, at least 50% of which have a ClogP of at least 3.

In addition, it is advantageous if the fragrance is comprised of perfume raw materials which have a molecular weight of less than 200. Without wishing to be bound by theory, it appears that, above this threshold, the likelihood of complexation decreases, so that this represents another factor which may assist in preferential complexation of a given molecular species.

Examples of PRMs having a ClogP of at least 3 and with molecular weights of less than 200 include but are not limited to: citronellol, Ethyl cinnamate, 2,4,6-Trimethylbenzaldehyde, 2,6-Dimethyl-2-heptanol, Diisobutylcarbinol, Ethyl salicylate, Phenethyl isobutyrate, Ethyl hexyl ketone, Propyl amyl ketone, Dibutyl ketone, Heptyl methyl ketone, 4,5-Dihydrotoluene, Caprylic aldehyde, Citral, Geranial, Isopropyl benzoate, Cyclohexanepropionic acid, Campholene aldehyde, Caprylic acid, Caprylic alcohol, Cuminaldehyde, 1-Ethyl-4-nitrobenzene, Heptyl formate, 4-Isopropylphenol, 2-Isopropylphenol, 3-Isopropylphenol, Allyl disulfide, 4-Methyl-1-phenyl-2-pentanone, 2-Propylfuran, Allyl caproate, Styrene, Isoeugenyl methyl ether, Indonaphthene, Diethyl suberate, L-Menthone, Menthone racemic, p-Cresyl isobutyrate, Butyl butyrate, Ethyl hexanoate, Propyl valerate, n-Pentyl propanoate, Hexyl acetate, Methyl heptanoate, trans-3,3,5-Trimethylcyclohexanol, 3,3,5-Trimethylcyclohexanol, Ethyl p-anisate, 2-Ethyl-1-hexanol, Benzyl isobutyrate, 2,5-Dimethylthiophene, Isobutyl 2-butenoate, Caprylnitrile, gamma-Nonalactone, Nerol, trans-Geraniol, 1-Vinylheptanol, Eucalyptol, 4-Terpinenol, Dihydrocarveol, Ethyl 2-methoxybenzoate, Ethyl cyclohexanecarboxylate, 2-Ethylhexanal, Ethyl amyl carbinol, 2-Octanol, 2-Octanol, Ethyl methylphenylglycidate, Diisobutyl ketone, Coumarone, Propyl isovalerate, Isobutyl butanoate, Isopentyl propanoate, 2-Ethylbutyl acetate, 6-Methyl-tetrahydroquinoline, Eugenyl methyl ether, Ethyl dihydrocinnamate, 3,5-Dimethoxytoluene, Toluene, Ethyl benzoate, n-Butyrophenone, alpha-Terpineol, Methyl 2-methylbenzoate, Methyl 4-methylbenzoate, Methyl 3, methylbenzoate, sec.Butyl n-butyrate, 1,4-Cineole, Fenchyl alcohol, Pinanol, cis-2-Pinanol, 2,4, Dimethylacetophenone, Isoeugenol, Safrole, Methyl 2-octynoate, o-Methylanisole, p-Cresyl methyl ether, Ethyl anthranilate, Linalool, Phenyl butyrate, Ethylene glycol dibutyrate, Diethyl phthalate, Phenyl mercaptan, Cumic alcohol, m-Toluquinoline, 6-Methylquinoline, Lepidine, 2-Ethylbenzaldehyde, 4-Ethylbenzaldehyde, o-Ethylphenol, p-Ethylphenol, m-Ethylphenol, (+)-Pulegone, 2,4-Dimethylbenzaldehyde, Isoxylaldehyde, Ethyl sorbate, Benzyl propionate, 1,3-Dimethylbutyl acetate, Isobutyl isobutanoate, 2,6-Xylenol, 2,4-Xylenol, 2,5-Xylenol, 3,5-Xylenol, Methyl cinnamate, Hexyl methyl ether, Benzyl ethyl ether, Methyl salicylate, Butyl propyl ketone, Ethyl amyl ketone, Hexyl methyl ketone, 2,3-Xylenol, 3,4, Xylenol.

Compositions according to the invention may also comprise a second fragrance. Advantageously, the second fragrance comprises PRMs at least 80% of which, preferably at least 90% of which have a boiling point of more than 300° C.—these fragrances essentially correspond to the "middle notes" and "base notes".

With reference to the foregoing discussion, it is also preferred that the molecular weights of the perfume raw materials comprised within the second fragrance are 200 or more.

Fulfilment of this condition may have the effect that the second fragrance is less likely to form complexes with the encapsulation material than the first fragrance. In the case that the first fragrance comprises "top notes", this may allow preferential entrapment and delayed release of the highly volatile fragrance.

Examples of PRMs corresponding to middles and base notes which have molecular weights of 200 or more include, but are not limited to: sandalore, Sorbitol, (S)-2-Aminopentanedioic acid, DL-Tartaric acid, Triethanolamine, (S)-alpha-Aminobenzenepropanoic acid, Adipic acid, Acetanilide, Coumarin, p-Hydroxybenzaldehyde, Azelaic acid, Methyl beta-naphthyl ketone.

Certain embodiments of the composition according to the present invention advantageously comprise at least 50% wt water. Preferably, they comprise at least 70% wt water, more preferably between 75 and 90% wt water.

Compositions according to the invention may comprise a volatile, non-aqueous solvent which has the ability to impart a refreshing skin-feel to a fragrance. On the other hand, as stated above, certain solvents such as alcohols may interfere with the entrapment materials. This effect may be suppressed when the volatile solvent is comprised within an aqueous solution at levels of less than 20% wt and preferably between 5 and 15% wt.

As used herein, the term "volatile non-aqueous solvent" includes solvents having a boiling point under 1 atm, of less than about 100° C., preferably less than about 90° C., more preferably less than about 80° C.

The volatile solvents for use herein will be safe for use on a wide range of substrates, especially human or animal skin or hair. Suitable volatile solvents for inclusion according to the invention include $C_3$–$C_{14}$ saturated and unsaturated, straight or branched chain hydrocarbons such as cyclohexane, hexane, heptane, isooctane, isopentane, pentane; ethers such as dimethyl ether, diethyl ether; straight or branched chain alcohols and diols such as methanol, ethanol, propanol, isopropanol; aldehydes and ketones such as acetone; propellants, and mixtures thereof. Preferred volatile solvents are $C_1$–$C_4$ alcohols and mixtures thereof. More preferred for use herein are $C_1$–$C_4$ straight chain or branched chain alcohols for example methanol, ethanol, propanol, isopropanol and butanol and mixtures thereof, and most preferred for use herein is ethanol.

According to the second aspect of the invention, a personal care article is provided comprising a substrate and a composition as defined above.

The weight ratio of substrate:composition according to the first aspect of the invention may be in the range 1:0.1 to 1:10, is preferably in the range 1:0.2 to 1:8.0 and is more preferably 1:3.1.

The composition according to the first aspect of the invention may be introduced onto or into the substrate by any method known to those skilled in the art, such as by dipping the substrate into the composition, spraying the composition onto or into the substrate or pumping the composition into the substrate.

Substrates which may be incorporated into personal cleansing articles according to the invention are preferably water insoluble and may comprise woven, nonwoven, hydroentangled and air entangled material, natural or synthetic sponge, polymeric netted meshes, or mixtures of these materials. Preferably, the substrate comprises nonwoven material.

The substrate may comprise natural materials, synthetic materials or a mixture of the two.

Included within the term "natural materials" are those directly derived from plants, animals and insects and those which comprise products of plants, animals, and insects. Included within the term "synthetic materials" are those obtained primarily from man-made materials or from natural materials which have been further altered.

In making a nonwoven substrate, the conventional starting material usually comprises fibrous synthetic or natural textile-length fibers, or mixtures thereof. Nonlimiting examples of natural materials useful in the present invention include silk fibers, keratin fibers and cellulosic fibers. Nonlimiting examples of keratin fibers include those selected from the group consisting of wool fibers, camel hair fibers, and the like. Nonlimiting examples of cellulosic fibers include those selected from the group consisting of wood pulp fibers, cotton fibers, hemp fibers, jute fibers, flax fibers, and mixtures thereof. Nonlimiting examples of synthetic materials useful in the present invention include those selected from the group consisting of acetate fibers, acrylic fibers, cellulose ester fibers, modacrylic fibers, polyamide fibers, polyester fibers, polyolefin fibers, polyvinyl alcohol fibers, rayon fibers, polyurethane foam, and mixtures thereof. Examples of some of these synthetic materials include acrylics such as acrilan, creslan, and the acrylonitrile-based fiber, orlon; cellulose ester fibers such as cellulose acetate, amel, and acele; polyamides such as nylons (e.g., nylon 6, nylon 66, nylon 610, and the like); polyesters such as fortrel, kodel, and the polyethylene terephthalate fiber, dacron; polyolefins such as polypropylene, polyethylene; polyvinyl acetate fibers; polyurethane foams and mixtures thereof. These and other suitable fibers and the nonwoven materials prepared therefrom are generally described in Riedel, "Nonwoven Bonding Methods and Materials," Nonwoven World (1987); the Encyclopedia Americana, vol. 11, pp. 147–153, and vol. 26, pp. 566–581 (1984); U.S. Pat. No. 4,891,227 and U.S. Pat. No. 4,891,228. Nonwoven substrates made from natural materials consist of webs or sheets most commonly formed on a fine wire screen from a liquid suspension of the fibers. See C. A. Hampel et al., The Encyclopedia of Chemistry, third edition, 1973, pp. 793–795 (1973); The Encyclopedia Americana, vol. 21, pp. 376–383 (1984); and G. A. Smook, Handbook of Pulp and Paper Technologies, Technical Association for the Pulp and Paper Industry (1986).

Methods of making nonwoven substrates are well known in the art. Generally, these nonwoven substrates can be made by air-laying, water-laying, meltblowing, coforming, spin-bonding, or carding processes in which the fibers or filaments are first cut to desired lengths from long strands, passed into a water or air stream, and then deposited onto a screen through which the fiber-laden air or water is passed. The resulting layer, regardless of its method of production or composition, is then subjected to at least one of several types of bonding operations to anchor the individual fibers together to form a self-sustaining web. In the present invention the nonwoven layer can be prepared by a variety of processes including hydroentanglement, thermally bonding or thermo-bonding, and combinations of these processes. Moreover, the substrates of the present invention can consist of a single layer or multiple layers. In addition, a multilayered substrate can include films and other nonfibrous materials.

The substrate can be made into a wide variety of shapes and forms including flat pads, thick pads, thin sheets, ball-shaped implements, irregularly shaped implements, and having sizes ranging from a surface area of 6.25 $cm^2$ (a square inch) to about hundreds of square centimetres. The exact size will depend upon the desired use and product characteristics. Especially convenient are square, circular, rectangular, or oval pads having a surface area of from about 6.25 $cm^2$ (1 $in^2$) to about 900 $cm^2$.

According to the third aspect of the invention, a personal care article is provided comprising a substrate, as defined hereinabove, and a composition, the composition comprising a fragrance-releasing complex, as defined hereinabove, and more than 50% wt water, preferably between 80 and 90% wt water.

Advantageously, the personal care articles according to the second and third aspects of the invention may be packaged as wet wipes in water-proof packaging.

The compositions and personal care articles according to the present invention may comprise a wide range of optional ingredients, such as active ingredients, sunscreens, surfactants and other materials.

The compositions and personal care articles of the present invention can comprise a safe and effective amount of one or more active ingredients or pharmaceutically-acceptable salts thereof. The term "safe and effective amount" as used herein, means an amount of an active ingredient high enough to modify the condition to be treated or to deliver the desired skin benefit, but low enough to avoid serious side effects, at a reasonable benefit to risk ratio within the scope of sound medical judgment. What is a safe and effective amount of the active ingredient will vary with the specific active, the ability of the active to penetrate through the skin, the age, health condition, and skin condition of the user, and other like factors.

Anti-Acne Actives: Examples of useful anti-acne actives include the keratolytics such as salicylic acid (o-hydroxybenzoic acid), derivatives of salicylic acid such as 5-octanoyl salicylic acid, and resorcinol; retinoids such as retinoic acid and its derivatives (e.g., cis and trans); sulfur-containing D and L amino acids and their derivatives and salts, particularly their N-acetyl derivatives, a preferred example of which is N-acetyl-L-cysteine; lipoic acid; antibiotics and antimicrobials such as benzoyl peroxide, octopirox, tetracycline, 2,4,4'-trichloro-2'-hydroxy diphenyl ether, 3,4,4'-trichlorobanilide, azelaic acid and its derivatives, phenoxyethanol, phenoxypropanol, phenoxyisopropanol, ethyl acetate, clindamycin and meclocycline; sebostats such as flavonoids; and bile salts such as scymnol sulfate and its derivatives, deoxycholate, and cholate.

Anti-Wrinkle and Anti-Skin Atrophy Actives: Examples of antiwrinkle and anti-skin atrophy actives include retinoic acid and its derivatives (e.g., cis and trans); retinol; retinyl esters; niacinamide, salicylic acid and derivatives thereof; sulfur-containing D and L amino acids and their derivatives and salts, particularly the N-acetyl derivatives, a preferred example of which is N-acetyl-L-cysteine; thiols, e.g. ethane thiol; hydroxy acids, phytic acid, lipoic acid; lysophosphatidic acid, and skin peel agents (e.g., phenol and the like).

Non-Steroidal Anti-Inflammatory Actives (NSAIDS): Examples of NSAIDS include the following categories: propionic acid derivatives; acetic acid derivatives; fenamic acid derivatives; biphenylcarboxylic acid derivatives; and oxicams. All of these NSAIDS are fully described in U.S. Pat. No. 4,985,459. Examples of useful NSAIDS include acetyl salicylic acid, ibuprofen, naproxen, benoxaprofen, flurbiprofen, fenoprofen, fenbufen, ketoprofen, indoprofen, pirprofen, carprofen, oxaprozin, pranoprofen, miroprofen, tioxaprofen, suprofen, alminoprofen, tiaprofenic acid, fluprofen and bucloxic acid. Also useful are the steroidal anti-inflammatory drugs including hydrocortisone and the like.

Topical Anesthetics: Examples of topical anesthetic drugs include benzocaine, lidocaine, bupivacaine, chlorprocaine, dibucaine, etidocaine, mepivacaine, tetracaine, dyclonine, hexylcaine, procaine, cocaine, ketamine, pramoxine, phenol, and pharmaceutically acceptable salts thereof.

Artificial Tanning Agents and Accelerators: Examples of artificial tanning agents and accelerators include dihydroxyacetaone, tyrosine, tyrosine esters such as ethyl tyrosinate, and phospho-DOPA.

Antimicrobial and Antifungal Actives: Examples of antimicrobial and antifungal actives include β-lactam drugs, quinolone drugs, ciprofloxacin, norfloxacin, tetracycline, erythromycin, amikacin, 2,4,4'-trichloro-2'-hydroxy diphenyl ether, 3,4,4'-trichlorobanilide, phenoxyethanol, phenoxy propanol, phenoxyisopropanol, doxycycline, capreomycin, chlorhexidine, chlortetracycline, oxytetracycline, clindamycin, ethambutol, hexamidine isethionate, metronidazole, pentamidine, gentamicin, kanamycin, lineomycin, methacycline, methenamine, minocycline, neomycin, netilmicin, paromomycin, streptomycin, tobramycin, miconazole, tetracycline hydrochloride, erythromycin, zinc erythromycin, erythromycin estolate, erythromycin stearate, amikacin sulfate, doxycycline hydrochloride, capreomycin sulfate, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, amanfadine hydrochloride, amanfadine sulfate, octopirox, parachlorometa xylenol, nystatin, tolnaftate, zinc pyrithione, clotrimazole and methyl- and ethylparaben.

Preferred examples of actives useful herein include those selected from the group consisting of salicylic acid, benzoyl peroxide, 3-hydroxy benzoic acid, glycolic acid, lactic acid, 4-hydroxy benzoic acid, acetyl salicylic acid, 2-hydroxybutanoic acid, 2-hydroxypentanoic acid, 2-hydroxyhexanoic acid, cis-retinoic acid, trans-retinoic acid, retinol, phytic acid, N-acetyl-L-cysteine, lipoic acid, azelaic acid, arachidonic acid, benzoylperoxide, tetracycline, ibuprofen, naproxen, hydrocortisone, acetominophen, resorcinol, phenoxyethanol, phenoxypropanol, phenoxyisopropanol, 2,4,4'-trichloro-2'-hydroxy diphenyl ether, 3,4,4'-trichlorocarbanilide, octopirox, lidocaine hydrochloride, clotrimazole, miconazole, neocycin sulfate, and mixtures thereof.

Cooling agents: examples include but are not limited to trimethyl isopropyl butanamide, ethyl methane carboxamide, menthol, and menthyl lactate.

Sunscreen Actives: Also useful herein are sunscreening actives. A wide variety of sunscreening agents are described in U.S. Pat. Nos. 5,087,445, 5,073,372, 5,073,371 and Segarin, et al., at Chapter VIII, pages 189 et seq., of *Cosmetics Science and Technology*. Nonlimiting examples of sunscreens which are useful in the compositions of the present invention are those selected from the group consisting of 2-ethylhexyl p-methoxycinnamate, 2-ethylhexyl N,N-dimethyl-p-aminobenzoate, p-aminobenzoic acid, 2-phenyl-benzimidazole-5-sulfonic acid, octocrylene, oxybenzone, homomenthyl salicylate, octyl salicylate, 4,4'-methoxy-t-butyldibenzoylmethane, 4-isopropyl dibenzoylmethane, 3-benzylidene camphor, 3-(4-methylbenzylidene) camphor, titanium dioxide, zinc oxide, silica, iron oxide, and mixtures thereof. Still other useful sunscreens are those disclosed in U.S. Pat. No. 4,937,370 and U.S. Pat. No. 4,999,186. Especially preferred examples of these sunscreens include those selected from the group consisting of 4-N,N-(2-ethylhexyl)methylaminobenzoic acid ester of 2,4-dihydroxybenzophenone, 4-N,N-(2-ethylhexyl)methylaminobenzoic acid ester with 4-hydroxydibenzoylmethane, 4-N,N-(2-ethylhexyl)-methylaminobenzoic acid ester of 2-hydroxy-4-(2-hydroxyethoxy)benzophenone, 4-N,N-(2-ethylhexyl)-methylaminobenzoic acid ester of 4-(2-hydroxyethoxy) dibenzoylmethane, and mixtures thereof. Exact amounts of sunscreens which can be employed will vary depending upon the sunscreen chosen and the desired Sun Protection Factor (SPF) to be achieved. SPF is a commonly used measure of photoprotection of a sunscreen against erythema. See *Federal Register*, Vol. 43, No. 166, pp. 38206–38269, Aug. 25, 1978.

Nonlimiting examples of preferred actives useful herein include those selected from the group consisting of salicylic acid, benzoyl peroxide, niacinamide, cis-retinoic acid, trans-retinoic acid, retinol, retinyl palmitate, phytic acid, N-acetyl L-cysteine, azelaic acid, lipoic acid, resorcinol, lactic acid, glycolic acid, ibuprofen, naproxen, hydrocortisone, phenoxyethanol, phenoxypropanol, phenoxyisopropanol, 2,4,4,'-trichloro-2'-hydroxy diphenyl ether, 3,4,4'-trichlorocarbanilide, 2-ethylhexyl p-methoxycinnamic acid, oxybenzone, 2-phenylbenzimidozole-5-sulfonic acid, dihydroxyacetone, and mixtures thereof.

The compositions and personal care articles according to the present invention can also optionally comprise one or more anionic and/or cationic surfactants, provided these materials do not interfere with the entrapment or encapsulation materials.

The compositions and personal care articles of the present invention can comprise a wide range of other optional components. These additional components should be pharmaceutically acceptable. The *CTFA Cosmetic Ingredient Handbook*, Second Edition, 1992, describes a wide variety of nonlimiting cosmetic and pharmaceutical ingredients commonly used in the skin and hair care industry, which are suitable for use in the compositions of the present invention. Nonlimiting examples of functional classes of ingredients are described at page 537 of this reference. Examples of these and other functional classes include: abrasives, absorbents, anticaking agents, antioxidants, vitamins, binders, biological additives, buffering agents, bulking agents, chelating agents, chemical additives, colorants, cosmetic astringents, cosmetic biocides, denaturants, drug astringents, external analgesics, film formers, fragrance components, humectants, opacifying agents, pH adjusters, preservatives, propellants, reducing agents and skin bleaching agents.

Compositions according to the invention may be manufactured by mixing first fragrance with the entrapment material in a first step for a sufficient period of time to allow entrapment, typically about an hour, then adding the encapsulation material in a second step and mixing again for a sufficient period to allow encapsulation, typically about 15 minutes.

If water is present, it is preferably mixed with the entrapment material in a pre-mixing step, prior to addition of the first fragrance in the first step.

If a second fragrance is present, it is preferably mixed with the pre-encapsulated complex in a third step. By doing this, it does not have a chance to compete for association with the entrapment material, since it is added later, and may also be prevented from doing so by the encapsulation material.

If a volatile non-aqueous solvent is present, it is preferably added in a fourth step. This has the advantage that the solvent is less likely to interfere with the entrapment materials if they are already pre-complexed.

Personal care articles according to the invention may be manufactured by applying compositions according to the invention to a substrate in one of the ways defined above and in a ratio as defined above.

Compositions according to the invention may be applied directly to the skin or hair or may be applied via a personal care article according to the invention. On application, the fragrance-releasing complex will typically become freed from encapsulation by the encapsulation material, following which fragrance release may be triggered by contact with materials on the skin etc. as described above.

All documents cited are, in relevant part, incorporated herein by reference; the citation of any document is not to be construed as an admission that it is prior art with respect to the present invention.

EXAMPLES

The following examples further describe and demonstrate the preferred embodiments within the scope of the present invention. The examples are given solely for the purpose of illustration, and are not to be construed as limitations of the present invention since many variations thereof are possible without departing from its scope.

Example 1

| Raw Materials | % w/w |
| --- | --- |
| Ethanol | 10.00 |
| Water | 88.05 |
| Methyl Beta Cyclodextrin | 0.50 |
| PEG 60, hydrogenated castor oil | 0.40 |
| Fragrance 2 | 0.07 |
| Fragrance 1 | 0.13 |
| Sodium Benzoate | 0.2 |
| Tetra Sodium EDTA | 0.1 |
| Hydrochloric Acid 1 M (used to adjust pH to approx 5.5) | 0.56 |

Where Fragrance 1 is Citronellol (molecular weight = 156, ClogP = 3.25) and Fragrance 2 is Sandalore (Molecular weight = 210, ClogP = 4.7)

Manufacturing Method
1. To water add sodium benzoate, tetrasodium edta and hydrochloric acid. Stir until dissolved.
2. Add methyl beta cyclodextrin and Fragrance 1 and stir continuously for 1 hour
3. Add PEG-60 hydrogenated caster oil and continually stir for a further 10 minutes
4. Add Fragrance 2 and stir for a further 5 minutes.
5. Add ethanol and mix for a further 10 minutes.
6. Transfer to appropriate container Addition of Composition to Substrate to Make a Wet Wipe A substrate comprising a 17 cm×24.5 cm piece of hydroentangled nonwoven (70% polyester; 30% rayon; basis weight of 64.0 gm$^{-2}$; supplied by BBA Nonwovens of Bethune, S.C., USA under the name Snotox™) is sprayed with composition at a weight ratio of 3.1 (composition): 1 (wipe) weight level. It is then sealed in a water-tight container.

Example 2

| Raw Materials | % w/w |
| --- | --- |
| Alcohol | 10 |
| Water | 85.19 |
| Fragrance 1 | 0.266 |
| Fragrance 2 | 0.134 |
| Gamma Cyclodextrin | 1 |
| PEG 40 hydrogenated Caster oil | 0.4 |
| Sodium Benzoate | 0.2 |
| Hydrochloric Acid (1 molar) | 0.56 |
| Benzyl Alcohol | 0.25 |
| Tetrasodium EDTA | 0.1 |

The method of manufacture was as in Example 1.

Example 3

| Raw Materials | % w/w |
| --- | --- |
| Alcohol | 10 |
| Water | 81.14 |
| Fragrance 1 | 0.665 |
| Fragrance 2 | 0.335 |
| Methylated Beta cyclodextrin | 5 |
| Polysorbate 20 | 2 |
| Sodium Benzoate | 0.2 |
| Hydrochloric Acid (1 molar) | 0.56 |
| Tetrasodium EDTA | 0.1 |

The method of manufacture was as in Example 1.

While particilar embodiments of the present invention have been illustrated and described, it would be obvious to those skilled in the art that variouis other changes and modifications can be made without departing from the spirit and scope of the invention. It is therefore intended to cover in the appended claims all such changes and modifications that are within the scope of this invention.

What is claimed is:

1. Composition comprising a fragrance-releasing complex of an entrapment material comprising a cyclic oligosaccharide and a fragrance; and an encapsulation material comprising a nonionic surfactant selected from the group consisting of partially or fully hydrogenated polyoxyethylene castor oil ethers or polyoxyethylene hardened castor oil ethers, polyethoxylated fatty alcohol surfactants, glycerol mono-fatty acid esters, fatty acid esters of polyethylene glycol, fluorocarbon surfactants and mixtures thereof, wherein the weight ratio of fragrance-releasing complex to encapsulation material is greater than 1.

2. Composition according to claim 1, wherein the weight ratio of fragrance-releasing complex to encapsulation material is in the range 1:0.1 to 1:0.9.

3. Composition according to claim 1, wherein the weight ratio of fragrance-releasing complex to encapsulation material is in the range 1:0.35 to 1:0.71.

4. Composition according to claim 1, wherein the non-ionic surfactant has a molecular weight above 400.

5. Composition according to claim 1, wherein the fragrance is a first fragrance and comprises perfume raw materials wherein at least 80% of which have a boiling point of less than or equal to 300° C.

6. Composition according to claim 5, wherein the first fragrance comprises perfume raw materials wherein at least 50% of which have a ClogP value of greater than or equal to 3.

7. Composition according to claim 5, wherein the first fragrance comprises perfume raw materials having a molecular weight of less than 200.

8. Composition according to claim 5 further comprising a second fragrance comprising perfume raw materials wherein at least 80% of which have a boiling point above 300° C.

9. Composition according to claim 8, wherein the second fragrance comprises perfume raw materials having a molecular weight of 200 or more.

10. Composition according to claim 1 having a water content of at least 50% wt.

11. Composition according to claim 10, wherein the water content is from 80 to 90% wt.

12. Composition according to claim 10 comprising less than 20% wt volatile non-aqueous solvent.

13. A personal care article comprising a substrate and a composition according to claim 1.

14. A personal care article according to claim 13, wherein the weight ratio of substrate to composition is in the range 1:0.1 to 1:10.

15. A personal care article according to claim 13 comprising more than 50% wt water.

16. A personal care article according to claim 13, wherein the substrate is a nonwoven fabric.

17. A wet wipe comprising the personal care article of claim 16.

* * * * *